US009182586B2

(12) United States Patent
Honda (10) Patent No.: US 9,182,586 B2
(45) Date of Patent: Nov. 10, 2015

(54) ENDOSCOPE

(71) Applicant: OLYMPUS MEDICAL SYSTEMS CORP., Tokyo (JP)

(72) Inventor: Kazuki Honda, Higashiyamato (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/313,300

(22) Filed: Jun. 24, 2014

(65) Prior Publication Data

US 2014/0346332 A1  Nov. 27, 2014

Related U.S. Application Data

(63) Continuation of application No. PCT/JP2013/077094, filed on Oct. 4, 2013.

(30) Foreign Application Priority Data

Nov. 5, 2012  (JP) ................................. 2012-243699

(51) Int. Cl.
| | |
|---|---|
| *G02B 23/26* | (2006.01) |
| *A61B 1/06* | (2006.01) |
| *G02B 23/24* | (2006.01) |
| *G01B 11/14* | (2006.01) |
| *G01J 1/04* | (2006.01) |
| *G01J 1/42* | (2006.01) |

(Continued)

(52) U.S. Cl.
CPC ............ *G02B 23/26* (2013.01); *A61B 1/00096* (2013.01); *A61B 1/00177* (2013.01); *A61B 1/00179* (2013.01); *A61B 1/00181* (2013.01); *A61B 1/0615* (2013.01);

(Continued)

(58) Field of Classification Search
CPC .. G02B 23/26; A01B 12/006; A61B 1/00177; G01B 11/14
See application file for complete search history.

(56) References Cited

U.S. PATENT DOCUMENTS 8,926,502 B2 * 1/2015 Levy et al. .................... 600/170
9,039,605 B2 * 5/2015 Sone ............................. 600/117

(Continued)

FOREIGN PATENT DOCUMENTS

| EP | 2385406 A1 | 11/2011 |
|---|---|---|
| JP | 2007-135756 A | 6/2007 |

(Continued)

OTHER PUBLICATIONS

International Search Report dated Nov. 5, 2013 issued in PCT/JP2013/077094.

(Continued)

*Primary Examiner* — Tony Ko
(74) *Attorney, Agent, or Firm* — Scully, Scott, Murphy & Presser, P.C.

(57) ABSTRACT

An endoscope includes: a first objective lens that causes an image of a first object to be observed to be formed; a second objective lens that causes an image of a second object to be observed to be formed; a light guide that guides illuminating light from a light source to an insertion portion; a light distribution member that distributes light from the light guide between a first observation direction and a second observation direction; a light amount varying portion for changing light amount proportions with respect to light emitted in the first observation direction and light emitted in the second observation direction; a distance detection portion that measures a second distance between the second objective lens and an object to be observed in the second observation direction; and a control portion that controls the light amount varying portion based on a second distance signal.

13 Claims, 8 Drawing Sheets

(51) Int. Cl.
G02B 26/02 (2006.01)
A61B 1/00 (2006.01)
(52) U.S. Cl.
CPC ............ *A61B 1/0623* (2013.01); *G01B 11/14* (2013.01); *G01J 1/0425* (2013.01); *G01J 1/0448* (2013.01); *G01J 1/42* (2013.01); *G02B 23/243* (2013.01); *G02B 23/2423* (2013.01); *G02B 23/2469* (2013.01); *G02B 26/02* (2013.01)

(56) References Cited

U.S. PATENT DOCUMENTS

2007/0112247 A1 5/2007 Hirata
2011/0273784 A1 11/2011 Mizusawa

FOREIGN PATENT DOCUMENTS

| JP | 2008-228810 A | 10/2008 |
| JP | 2010-169792 A | 8/2010 |
| JP | 2011-019692 A | 2/2011 |
| JP | 2011-152202 A | 8/2011 |
| JP | 5138125 B2 | 11/2012 |
| WO | WO 2010/084914 A1 | 7/2010 |
| WO | WO 2011/055641 A1 | 5/2011 |
| WO | 2012132598 A1 | 10/2012 |
| WO | WO 2012/132598 A1 | 10/2012 |

OTHER PUBLICATIONS

Japanese Office Action dated Aug. 19, 2014 received in JP 2014-528750 with English Translation.

\* cited by examiner

ENDOSCOPE

CROSS REFERENCE TO RELATED APPLICATION

This application is a continuation application of PCT/JP2013/077094 filed on Oct. 4, 2013 and claims benefit of Japanese Application No. 2012-243699 filed in Japan on Nov. 5, 2012, the entire contents which are incorporated herein by this reference.

BACKGROUND OF THE INVENTION

1. Field of the Invention

This invention relates to an endoscope with which a front field of view and a lateral field of view can be observed simultaneously.

2. Description of the Related Art

Endoscopes have been widely used in medical fields and industrial fields in recent years. An endoscope can observe an inside of a subject by inserting an elongated insertion portion into the subject. Various types of such endoscopes have been proposed and put into practical use including, for example, a front-view type endoscope in which an observation lens or an illumination lens is provided in a distal end face of a distal end portion that is provided on a distal end side of an insertion portion, and a side-view type endoscope in which an observation lens or an illumination lens is provided at a part of a side face of a distal end portion of an insertion portion.

Furthermore, recently, in order to widen the observation range, various endoscopes that are configured to enable observation not only in a field of view in front of a distal end portion of an insertion portion, but also in a field of view in a circumferential direction that is laterally located along the circumference of the outer circumferential side face of the distal end portion at the same time have been proposed in, for example, Japanese Patent Application Laid-Open Publication No. 2011-152202 and Japanese Patent Application Laid-Open Publication No. 2008-228810, and put into practical use.

Such kinds of endoscopes have a configuration that includes front illumination means for illuminating a front field of view range, and lateral illumination means for illuminating an entire lateral circumference field-of-view range. As the aforementioned lateral illumination means, for example, a device has been proposed which illuminates the entire lateral circumference by scattering an illuminating light that has been optically guided from a light source to a distal end side in the longitudinal direction of an insertion portion of the endoscope using a light guide fiber or the like in the radial direction of the insertion portion.

Further, some conventional endoscopes include means for measuring the amount of reflected light from an observation target and detecting a luminance distribution of the observation target. In an endoscope disclosed in, for example, Japanese Patent Application Laid-Open Publication No. 2011-019692, luminance distribution information that is detected in this manner is used for calculating a photographing distance between the distal end portion of the insertion portion and the observation target.

SUMMARY OF THE INVENTION

An endoscope according to one aspect of the present invention includes: a first objective lens that is disposed in an insertion portion to be inserted into a lumen, and forms an image of an object to be observed that is in a first observation direction; a second objective lens that is disposed in the insertion portion, and forms an image of an object to be observed that is in a second observation direction that is different from the first observation direction; a light guide that guides an illuminating light that is emitted from a light source to the insertion portion; a light distribution member that distributes light from the light guide between the first observation direction and the second observation direction; light amount varying means for changing proportions of light amounts with respect to illuminating light emitted in the first observation direction and illuminating light emitted in the second observation direction that the light distribution member distributes; a distance detection portion that measures a second distance between the second objective lens and an object to be observed that is in the second observation direction; and a control portion that controls the light amount varying means based on a signal relating to the second distance that is outputted from the distance detection portion.

DETAILED DESCRIPTION OF THE PREFERRED EMBODIMENTS

Preferred embodiments of the present invention are described hereunder with reference to the accompanying drawings. Note that in some cases the respective components in the respective drawings used for the following description are displayed in a different contraction scale so as to be shown in a size that is recognizable in the drawings. Accordingly, the present invention is not limited only to the quantity of components, the shapes of components, the ratios between the sizes of components, and the relative positional relationship between the respective components illustrated in the drawings.

First Embodiment

Figure 1:
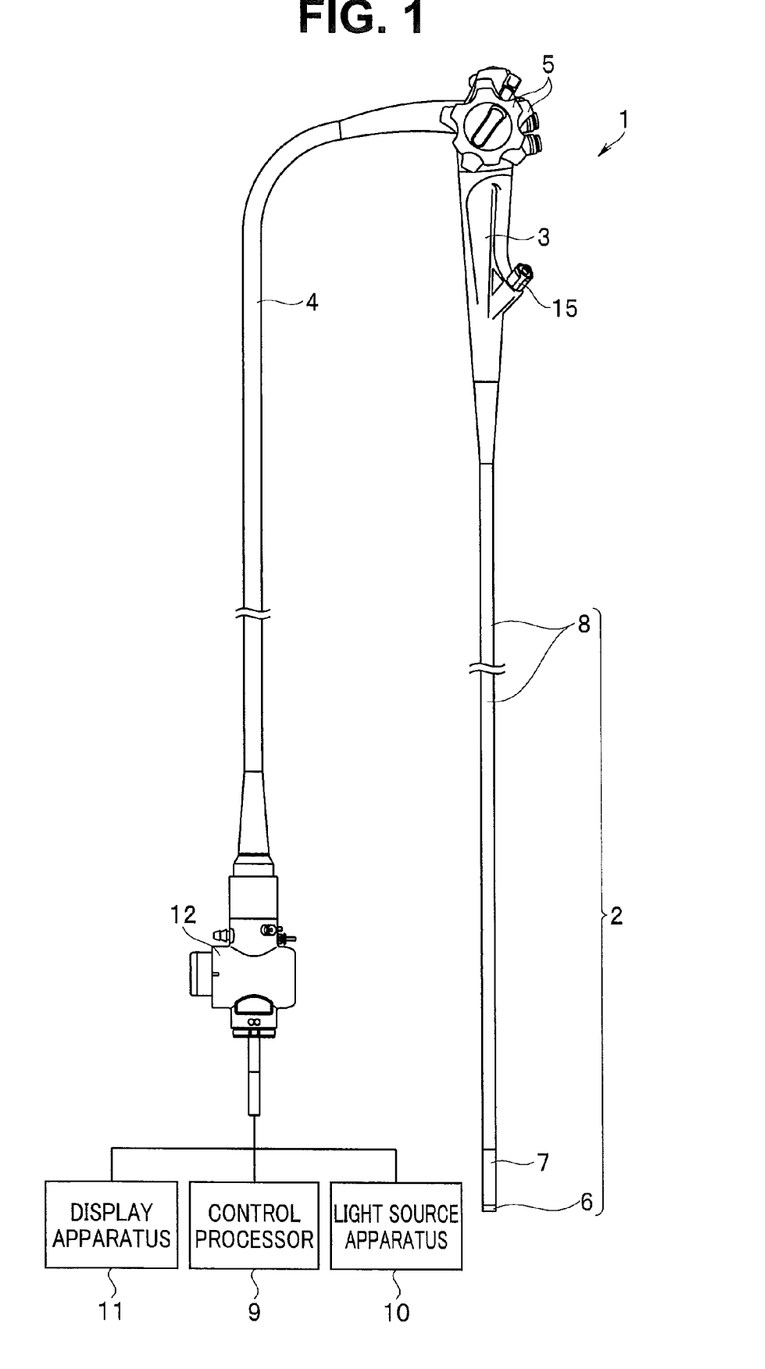
FIG. 1 is a schematic configuration diagram illustrating the overall configuration of an endoscope according to a first embodiment of the present invention.
Figure 2:
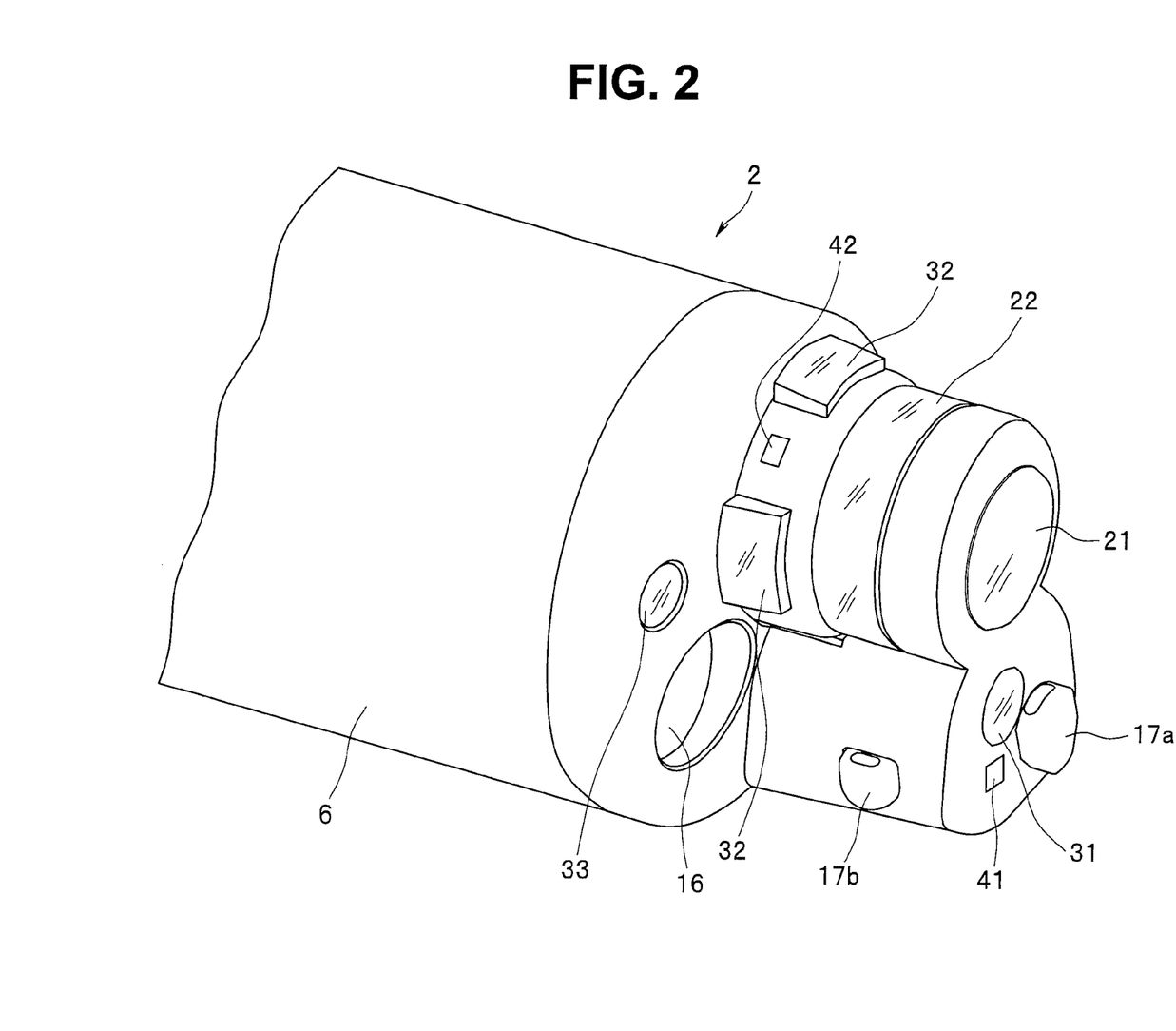
FIG. 2 is an enlarged perspective view of a principal portion that illustrates, in an enlarged manner, a distal end portion of an insertion portion of the endoscope shown in FIG. 1.
Figure 3:
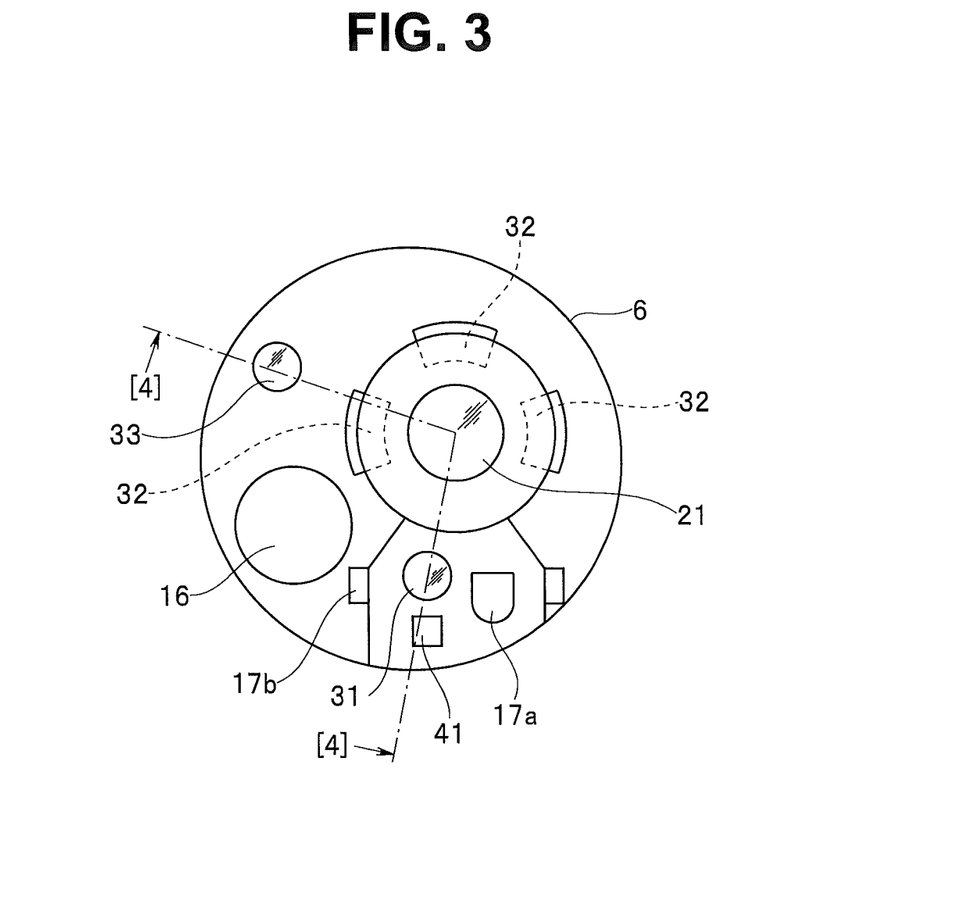
FIG. 3 is a front view of the distal end portion of the insertion portion shown in FIG. 2.
Figure 4:
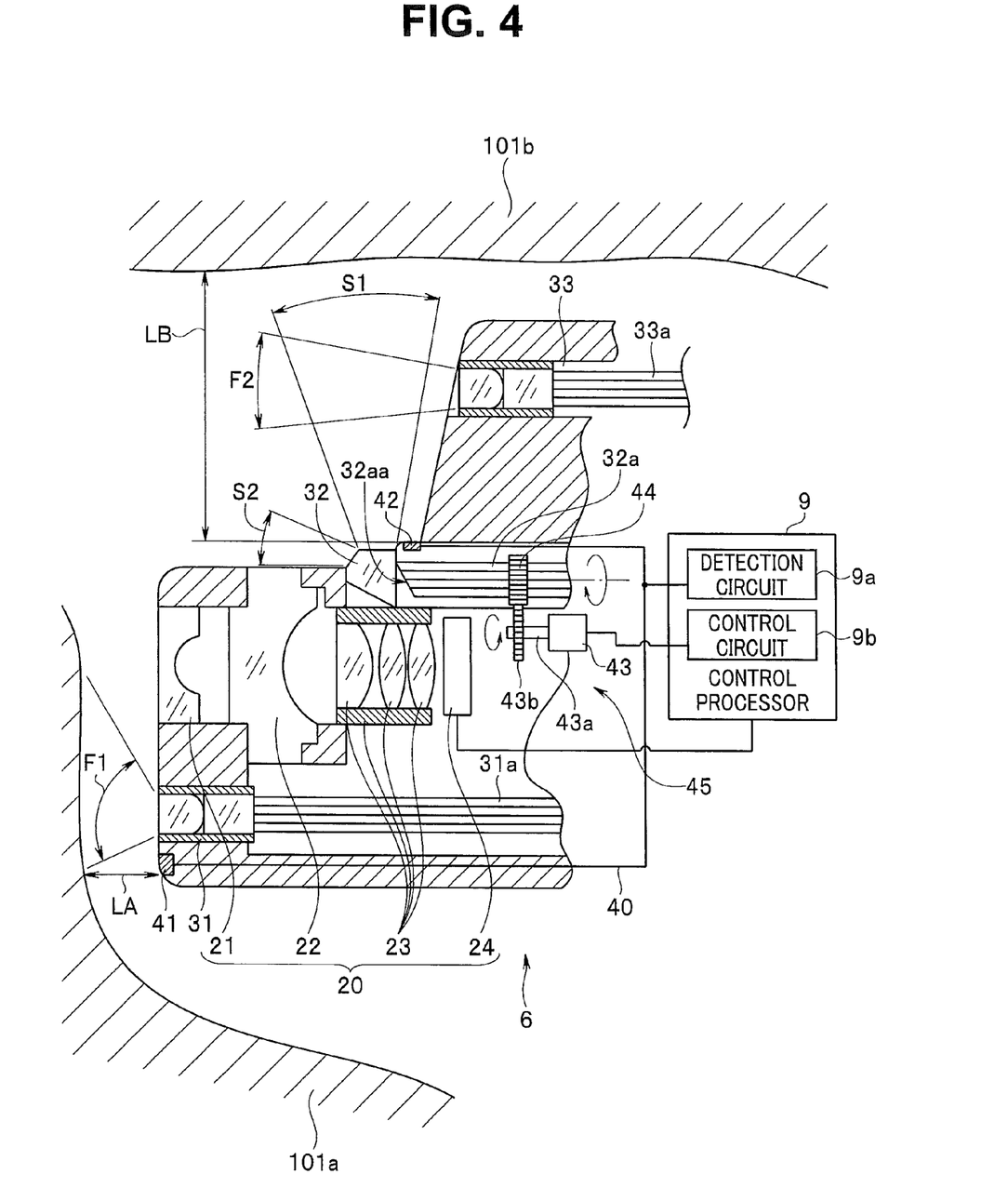
FIG. 4 is a cross-sectional view along a line [4]-[4] in FIG. 3.
Figure 5:
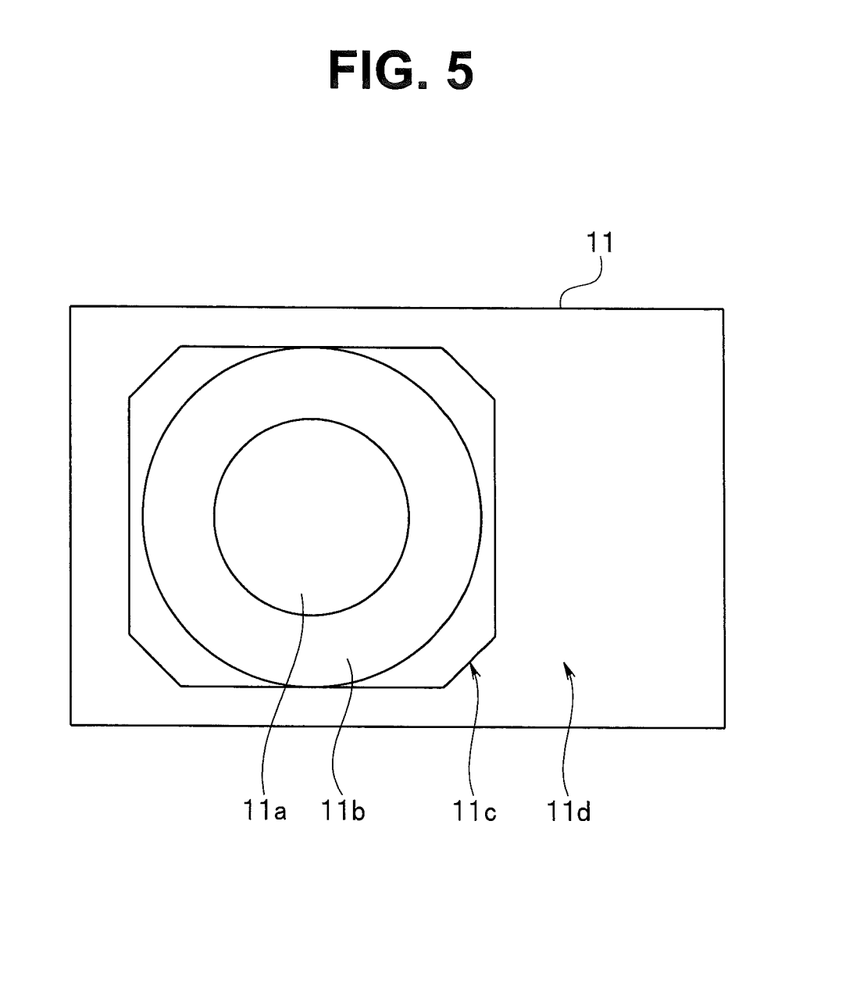
FIG. 5 is a conceptual diagram of a display screen of a display apparatus of an endoscope system shown in FIG. 1.
Figure 6:
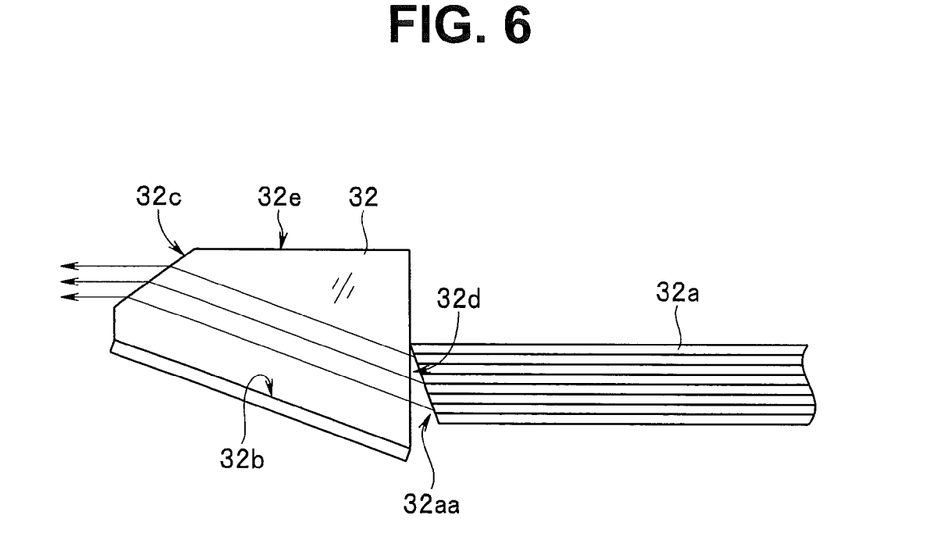
FIG. 6 is a schematic configuration diagram of a lateral illumination unit that illustrates an action of an illumination unit in the endoscope shown in FIG. 1, and shows the arrangement of a light guide when irradiating part of an illuminating light frontward using a lateral illumination lens.
Figure 7:
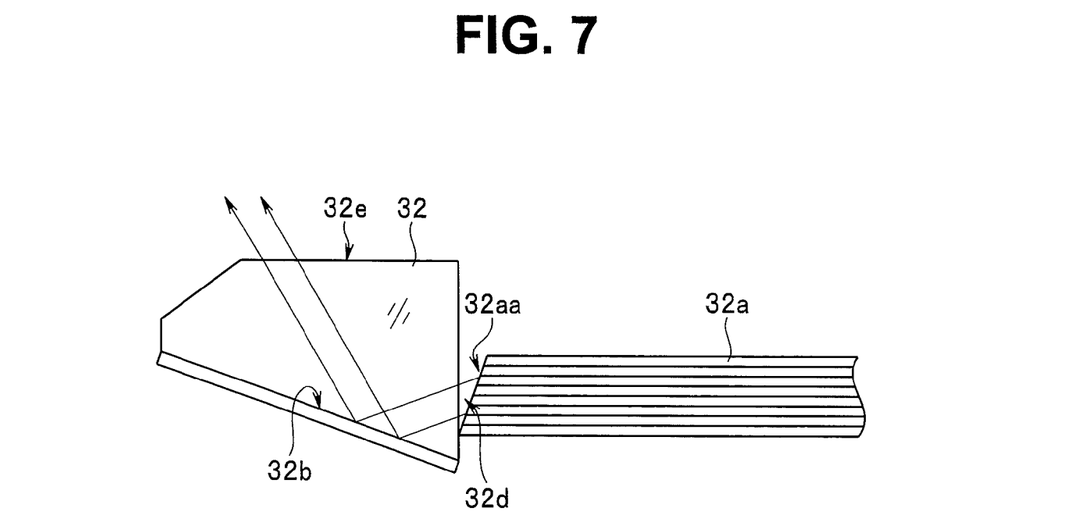
FIG. 7 is a schematic configuration diagram of the lateral illumination unit that illustrates an action of the illumination unit in the endoscope shown in FIG. 1, and shows the arrangement of the light guide when performing normal lateral irradiation using the lateral illumination lens.

First, a schematic configuration of an endoscope according to a first embodiment of the present invention is briefly described hereunder. FIG. 1 is a schematic configuration diagram illustrating the overall configuration of an endoscope according to the first embodiment of the present invention. FIG. 2 is an enlarged perspective view of a principal portion that illustrates, in an enlarged manner, a distal end portion of an insertion portion of the endoscope shown in FIG. 1. FIG. 3 is a front view of the distal end portion of the insertion portion shown in FIG. 2. FIG. 4 is a cross-sectional view along a line [4]-[4] in FIG. 3. FIG. 5 is a conceptual diagram of a display screen of a display apparatus of an endoscope system shown in FIG. 1. FIG. 6 and FIG. 7 are diagrams illustrating actions of an illumination unit in the endoscope shown in FIG. 1, of which FIG. 6 is a schematic configuration diagram of a lateral illumination unit that illustrates the arrangement of a light guide when irradiating part of an illuminating light frontward using a lateral illumination lens, and FIG. 7 is a schematic configuration diagram of the lateral illumination unit that illustrates the arrangement of the light guide when performing normal lateral irradiation using the lateral illumination lens.

As shown in FIG. 1, an endoscope 1 is mainly constituted by an elongated insertion portion 2 that is inserted into a body cavity or the like, an operation portion 3 that is connected to a proximal end side of the insertion portion 2, a universal cord 4 that is extended from the operation portion 3, and a connector portion 12 and the like provided at an end portion of the universal cord 4.

Note that, as shown in FIG. 2 to FIG. 4 and the like, the endoscope 1 of the present embodiment is a wide-field observation type endoscope having a configuration in which a front observation-use objective lens 21 and front illumination lenses 31 and 33 for front viewing are provided facing the front in a distal end face of a distal end portion 6 of the insertion portion 2, and a lateral observation-use objective lens 22 and a lateral illumination lens 32 are provided in the vicinity of the front observation-use objective lens 21, and which is configured to be capable of simultaneously observing a front field of view and a lateral field of view.

In this case, the front observation-use objective lens 21 is a first objective lens that forms an image of an observation target located in front of the insertion portion 2, and that is disposed on the distal end side of the insertion portion 2 that is inserted into a lumen. The lateral observation-use objective lens 22 is a circular second objective lens that forms an image of an observation target located at the side of the insertion portion 2, and that is disposed further on the proximal end side of the insertion portion 2 than the front observation-use objective lens 21 (first objective lens).

Returning to FIG. 1, the insertion portion 2 is constituted by the rigid distal end portion 6 that is provided at the distalmost end portion thereof, a bending portion 7 that is connected to the proximal end side of the distal end portion 6, and a flexible tube portion 8 constituted by a long tubular member having flexibility that is connected to the proximal end side of the bending portion 7.

As shown in FIG. 4, for example, an image pickup unit 20 and a plurality of illumination units are arranged inside the distal end portion 6 of the insertion portion 2. As shown in FIG. 2 and FIG. 3, for example, a treatment instrument channel opening 16, a front observation-use objective lens 21, illumination lenses 31, 32 and 33, and water feeding nozzles 17a and 17b are arranged in the distal end face of the distal end portion 6.

A treatment instrument channel (not shown in the drawings), a plurality of light guides (31a, 32a, 33a; see FIG. 4), and a signal cable 40 (see FIG. 4) and the like are inserted through the inside of the insertion portion 2. The treatment instrument channel is inserted through the inside of the insertion portion 2 from a treatment instrument channel opening 16 in the distal end face, and communicates with a treatment instrument insertion port 15 of the operation portion 3 (see FIG. 1). The plurality of light guides (31a, 32a, 33a) and the signal cable 40 extend from respective constituent units inside the distal end portion 6 of the insertion portion 2, are inserted through the insertion portion 2 and also through the inside of the universal cord 4 via the inside of the operation portion 3, and finally communicate with the connector portion 12 at the end of the universal cord 4. Note that the plurality of light guides (31a, 32a, 33a) are fiber bundles formed by bundling multiple light guide fibers for transmitting illuminating light. The plurality of light guides (31a, 32a, 33a) are light guiding means (described in detail later) for guiding an illuminating light emitted from a light source to the distal end side of the insertion portion 2.

An endoscope system including the endoscope 1 of the present embodiment is constructed by connecting the endoscope 1 to a control processor 9, a light source apparatus 10, and a display apparatus 11 or the like that are external apparatuses through the connector portion 12.

The operation portion 3 is a part that a user grasps when using the endoscope 1. Bending operation knobs 5 and a plurality of operation members that correspond to other various operations are arranged on the outer surface of the operation portion 3. In this case, for example, the bending operation knobs 5 are operation members that are configured to allow the user to bend the bending portion 7 of the insertion portion 2 in an arbitrary direction among the upward, downward, left, and right directions by rotating the bending operation knobs 5 using a finger or the like.

The treatment instrument insertion port 15 through which a treatment instrument (not shown in the drawings) or the like is inserted is formed at a position which is towards the distal end of the operation portion 3, and which is in the vicinity of the position where the operation portion 3 is connected with the insertion portion 2. The treatment instrument insertion port 15 communicates with the treatment instrument channel (not shown in the drawings) that is inserted through the inside of the insertion portion 2.

The light source apparatus 10 is an apparatus that emits an illuminating light. The control processor 9 is a signal processing apparatus that performs overall control of the endoscope system. The display apparatus 11 is a display portion that displays an endoscopic image based on an image pickup signal acquired by the endoscope 1. For example, an LCD panel is applied as the display apparatus 11.

The control processor 9, the light source apparatus 10, the display apparatus 11 and the endoscope 1 are connected through the connector portion 12. Thus, the control processor 9 performs the transmission of control signals, various detection signals, and acquired image signals and the like through the signal cable 40 (see FIG. 4) that is inserted through the inside of the endoscope 1. The control processor 9 also transmits processed image signals to the display apparatus 11, and causes the display apparatus 11 to display an endoscopic image and various kinds of information or the like. The plurality of light guides (31a, 32a, 33a) that are inserted through the inside of the endoscope 1 are connected to the light source apparatus 10. Thus, the endoscope system is configured so that an illuminating light from the light source apparatus 10 is guided to the plurality of light guides (31a, 32a, 33a) inside the universal cord 4, the operation portion 3, and the insertion portion 2 through the connector portion 12, and guided to a plurality of illumination units provided inside the distal end portion 6 of the insertion portion 2, and then emitted in respective predetermined directions through the respective illumination lenses 31, 32, and 33 in the distal end face.

The plurality of illumination units are constituted by the plurality of illumination lenses (31, 32, 33) and the plurality of light guides (31a, 32a, 33a) and the like. Among the plurality of illumination lenses (31, 32, 33), the illumination lens 31 is a light guiding body for front illumination that is a front illumination lens as a front illumination optical system that emits an illuminating light for illuminating a side that faces the distal end face of the endoscope 1, that is, the front of the distal end face of the endoscope 1. The illumination lens 32 is a light guiding body for lateral illumination that is a lateral illumination lens as a lateral illumination optical system that emits an illuminating light for illuminating a direction that is orthogonal to the distal end face of the endoscope 1, that is, the lateral direction with respect to the distal end face of the endoscope 1. The illumination lens 33 is a front auxiliary illumination optical system that emits an auxiliary illuminating light to perform auxiliary illumination with respect to the front of the endoscope 1.

The ends of the corresponding plurality of light guides (31a, 32a, 33a) are connected to the illumination lenses 31, 32, and 33, respectively, so that illuminating light guided from the light source apparatus 10 as described above can be incident thereon. Note that, among the aforementioned plurality of light guides, the light guide 31a is a first light guide for front illumination, the second light guide 32a is a second light guide for lateral illumination, and the light guide 33a is a third light guide for front auxiliary illumination.

The illumination lens 31 and the first light guide 31a constitute a front illumination unit. The illumination lens 32 and the second light guide 32a constitute a lateral illumination unit. The illumination lens 33 and the third light guide 33a constitute a front auxiliary illumination unit.

Among the plurality of illumination lenses, as shown in FIG. 2 and FIG. 3, the illumination lens for front illumination (hereunder, abbreviated to "front illumination lens) 31 is disposed in the vicinity of the front observation-use objective lens 21 in the front face of the distal end portion 6 of the insertion portion 2 so as to face in the same direction on substantially the same plane as the front observation-use objective lens 21. As shown in FIG. 4, a configuration is adopted in which the distal-end-side end face of the first light guide 31a is connected at the rear of the front illumination lens 31 so that illuminating light emitted from the first light guide 31a is made incident thereon to thereby irradiate the illuminating light in a predetermined range in front of the distal end portion 6 (range denoted by reference character F1 in FIG. 4). Since the first light guide 31a is inserted through the inside of the insertion portion 2 of the endoscope 1 as described above, the first light guide 31a is arranged parallel to the axial direction that is the longitudinal direction of the endoscope 1.

Note that, as shown in FIG. 2 and FIG. 3, a water feeding nozzle 17a is arranged in the vicinity of the front observation-use objective lens 21 and the front illumination lens 31 in the front face of the distal end portion 6. The water feeding nozzle 17a is a component that discharges a liquid or the like to clean the front face of the lenses 21 and 31. A configuration is adopted so that, in response to the user operating a predetermined operation member of the operation portion 3, a liquid or the like that was fed from a water feeding tank or the like that is not shown in the drawings passes through a water feed line (not shown) that is inserted through the universal cord 4, the operation portion 3, and the insertion portion 2, and is emitted by the water feeding nozzle 17a. A plurality of water feeding nozzles 17b are provided in the vicinity of the lateral observation-use objective lens 22 that is described later (see FIG. 2). The water feeding nozzles 17b are configured to be able to perform cleaning of the front face of the lateral observation-use objective lens 22 by having substantially the same configuration and functions as the water feeding nozzle 17a. Note that the configuration of the water feeding nozzles 17a and 17b and the like is similar to the configuration that is generally used in conventional endoscopes.

In addition, as shown in FIG. 2 to FIG. 4, a photometric sensor 41 is provided in the vicinity of the front illumination lens 31. The photometric sensor 41 receives reflected light from an observation target in front of the endoscope 1 and measures the amount of reflected light that is received. The photometric sensor 41 is provided in the front face of the distal end portion 6, and faces the front of the distal end portion 6. The photometric sensor 41 is electrically connected with a detection circuit 9a inside the control processor 9 that is connected to the connector portion 12, through the signal cable 40 that is inserted through the inside of the insertion portion 2, the operation portion 3 and the universal cord 4 until reaching the connector portion 12. The detection circuit 9a inside the control processor 9 performs an operation for calculating a distance (first distance) between the front observation-use objective lens 21 (first objective lens) and an observation target that is in front of the front observation-use objective lens 21 based on photometric information regarding the front field of view that is detected by the photometric sensor 41. Thus, the detection circuit 9a and the photometric sensor 41 constitute a first distance detection portion.

The front auxiliary illumination lens 33 that is used for auxiliary illumination of the front of the distal end portion 6 among the plurality of illumination lenses is configured in substantially the same manner as the front illumination lens 31, and is arranged in the distal end face of the distal end portion 6 so as to face in substantially the same direction as the front illumination lens 31. A distal-end-side end face of the third light guide 33a is disposed at the rear of the front auxiliary illumination lens 33. Thus, the configuration is such that illuminating light emitted from the third light guide 33a is made incident on the front auxiliary illumination lens 33, and the front auxiliary illumination lens 33 irradiates auxiliary illuminating light in a predetermined range in front of the distal end portion 6 (range denoted by reference character F2 in FIG. 4).

On the other hand, as shown in FIG. 2 and FIG. 3, the illumination lens for lateral illumination (hereunder, referred to as "lateral illumination lens") 32 among the plurality of illumination lenses is disposed at a position further towards the proximal end than the lateral observation-use objective lens 22 which is provided at a position that is further on the proximal end side than the front observation-use objective lens 21 in the distal end portion 6 of the insertion portion 2. The lateral illumination lens 32 is constituted by a transparent member or the like such as a prism that is formed so that the emission direction of illuminating light that was guided from the second light guide 32a can be changed to enable emission of the illuminating light towards the side of the insertion portion 2 and emission of part of the same illuminating light towards the front of the insertion portion 2. That is, the lateral illumination lens 32 functions as a light distribution member that distributes light from the second light guide 32a towards the front of the front observation-use objective lens 21 (first objective lens) and towards the side of the lateral observation-use objective lens 22 (second objective lens).

For that purpose, as shown in FIG. 6 and FIG. 7, the lateral illumination lens 32 is constituted by a prism composed of a polyhedron having at least a light incidence face 32d, a front emission face 32c, a lateral emission face 32e and a light scattering face 32b.

More specifically, in the lateral illumination lens 32, the light incidence face 32d is provided parallel to a face that is orthogonal to the axial direction of the distal end portion 6 of the insertion portion 2. A light emitting end face of the second light guide 32a contacts against the light incidence face 32d. Accordingly, the illuminating light of the second light guide 32a passes through the light incidence face 32d and is incident on the inside of the lateral illumination lens 32. In FIG. 6 and FIG. 7, the light scattering face 32b that is a light scattering portion that inclines towards the side of the light incidence face 32d is formed on a bottom face side between the light incidence face 32d and a face (front emission face 32c) that faces the light incidence face 32d. A surface treatment such that the light scattering face 32b can reflect and scatter illuminating light that is incident from the light incidence face 32d towards the inside of the lateral illumination lens 32 is executed on the inner surface of the light scattering face 32b. As the surface treatment executed on the light scattering face 32b, for example, a form can be adopted in which a so-called "satin-finish treatment" that forms concavities and convexities on an annular surface is first executed, and thereafter a coating material such as a reflective paint with high optical reflectivity is applied on the treatment surface. The light scattering face 32b in the light distribution member 32 is a light scattering portion that changes a ratio between illuminating light distributed to the front of the front observation-use objective lens 21 (first objective lens) and illuminating light distributed to the side of the lateral observation-use objective lens 22 (second objective lens) in accordance with the angle of incidence of the light from the second light guide 32a.

In the lateral illumination lens 32, the aforementioned front emission face 32c that inclines towards the front of the endoscope 1, and the lateral emission face 32e that faces towards the side of the endoscope 1 are formed, and light emitted from the lateral emission face 32e among the illuminating light from the light guide 32a serves as lateral illumination light. On the other hand, the lateral illumination lens 32 is configured so that part of the illuminating light is emitted towards the front from the front emission face 32c. As shown in FIG. 4, FIG. 6, FIG. 7 and the like, a configuration is adopted so that a distal-end-side end face 32aa of the second light guide 32a is disposed opposite the rear of the lateral illumination lens 32, and illuminating light emitted from the second light guide 32a is made incident on the rear side of the lateral illumination lens 32 so that the lateral illumination lens 32 can irradiate illuminating light in a predetermined range (range denoted by reference character S1 in FIG. 4) at the side of the distal end portion 6 and in a predetermined range (range denoted by reference character S2 in FIG. 4) in front of the distal end portion 6.

Since the second light guide 32a is inserted through the inside of the insertion portion 2 of the endoscope 1, similarly to the first light guide 31a and the third light guide 33a, the second light guide 32a is arranged parallel to the axial direction that is the longitudinal direction of the endoscope 1.

On the other hand, the distal-end-side end face 32aa of the second light guide 32a has a shape that has been diagonally cut at a predetermined angle with respect to the axial direction. Therefore, illuminating light that is emitted from the distal-end-side end face 32aa of the second light guide 32a is formed so that the emission angle thereof is different in comparison to a light guide having a normal end face shape (end face shape that has been cut parallel to a plane that is orthogonal to the axis). The emission angle can be freely changed by changing the orientation of the inclined face formed on the end face 32aa.

More specifically, as described later, a light amount varying mechanism 45 of the present embodiment is configured so as to be able to change the emission angle of illuminating light by causing the second light guide 32a to rotate around its axis by means of a driving force of a driving source 43, and thereby change the orientation of the distal-end-side end face 32aa of the second light guide 32a with respect to the light incidence face 32d of the lateral illumination lens 32.

For that purpose, a predetermined region in the vicinity of the distal end portion including at least the distal-end-side end face 32aa of the second light guide 32a is formed to be rotatable around its axis. Note that, although as means for changing an emission angle with respect to the axial direction of illuminating light emitted from the distal-end-side end face 32aa of the second light guide 32a, the distal-end-side end face 32aa has a form that has been diagonally cut, the means for changing the emission angle is not limited thereto, and other means may also be used. For example, completely the same effect can be obtained by adopting a configuration in which the distal-end-portion end face of the second light guide 32a is formed in the shape of a normal end face that has been cut in an orthogonal direction with respect to the axial direction, and a rod lens or the like is disposed with respect to the distal-end-portion end face.

The light amount varying mechanism 45 is arranged in the vicinity of the distal end portion of the second light guide 32a. The light amount varying mechanism 45 is light amount varying means for changing an emission angle of illuminating light that is made incident on the lateral illumination lens 32 from the second light guide 32a by causing a predetermined region in the vicinity of the distal end portion of the second light guide 32a to rotate by a predetermined rotation amount at a predetermined timing, to thereby change a ratio between light amounts of an illuminating light emitted to the front of the front observation-use objective lens 21 (first objective lens) and an illuminating light emitted to the side of the lateral observation-use objective lens 22 (second objective lens).

As shown in FIG. 4, the light amount varying mechanism 45 is constituted by the driving source 43 such as a motor or an actuator, and a driving force transmitting mechanism that is composed of a plurality of gear wheels or the like. For example, the driving force transmitting mechanism is constituted by a pinion gear 43b that is fixedly installed on a drive shaft 43a of the driving source 43, and a gear 44 that is integrally arranged in a predetermined region on the distal end side of the second light guide 32a and with which the pinion gear 43b intermeshes so as to cause the predetermined region on the distal end side of the second light guide 32a to rotate. The driving source 43 is configured so as to be subjected to driving control by a control circuit 9b that is a control portion inside the control processor 9 that is electrically connected to the driving source 43 via the signal cable 40.

On the other hand, as shown in FIG. 2 and FIG. 4, a photometric sensor 42 that receives reflected light from an observation target at the side of the endoscope 1 and measures the amount of reflected light that is received is provided in the vicinity of the lateral illumination lens 32. The photometric sensor 42 is arranged facing the side of the distal end portion 6. Similarly to the above described photometric sensor 41, the photometric sensor 42 is electrically connected to the detection circuit 9a inside the control processor 9 via the connector portion 12 through the signal cable 40 that is inserted through the endoscope 1. The detection circuit 9a inside the control processor 9 performs an operation for calculating a distance (second distance) between the lateral observation-use objective lens 22 (second objective lens) and an observation target that is at the side of the lateral observation-use objective lens 22 based on photometric information regarding the lateral field of view that is detected by the photometric sensor 42. Thus, the detection circuit 9a and the photometric sensor 42 constitute a second distance detection portion.

The control circuit 9b of the control processor 9 performs control to control driving of the driving source 43 of the light amount varying mechanism 45 based on signals relating to the first distance and the second distance that are outputted from the detection circuit 9a to thereby change the angle of the distal-end-side end face 32aa of the second light guide 32a with respect to the light incidence face 32d of the lateral illumination lens 32 and thus change the angle of incidence of illuminating light onto the lateral illumination lens 32 from the second light guide 32a.

In this case, FIG. 6 illustrates a state in which the inclined face of the distal-end-side end face 32aa of the second light guide 32a is set so as to face in the inward direction (face downward in FIG. 6). In this state, some of the illuminating light emitted from the second light guide 32a and incident on the lateral illumination lens 32 proceeds from the light incidence face 32d to the front emission face 32c, and is refracted at the front emission face 32c and irradiated to the front of the distal end portion of the endoscope 1.

In contrast, FIG. 7 illustrates a state in which the inclined face of the distal-end-side end face 32aa of the second light guide 32a is set so as to face outward (face upward in FIG. 7). In this state, the illuminating light emitted from the second light guide 32a and incident on the lateral illumination lens 32 proceeds from the light incidence face 32d to the lateral emission face 32e, and is irradiated to the side of the distal end portion of the endoscope 1 from the lateral emission face 32e.

As shown in FIG. 4, the image pickup unit 20 is constituted by the front observation-use objective lens 21, the lateral observation-use objective lens 22, a rear group optical system 23 including a plurality of optical lenses and a lens holding barrel, and an image pickup device 24 that is a photoelectric conversion element such as a charge coupled device, and the like. According to this configuration, an observation image of the front field of view is formed in a predetermined region on a light receiving surface of the image pickup device 24 via the front observation-use objective lens 21 and the rear group optical system 23. Concurrently therewith, an observation image of the lateral field of view is formed in a predetermined region on the light receiving surface of the image pickup device 24 via the lateral observation-use objective lens 22 and the rear group optical system 23. Upon receiving these images, the image pickup device 24 performs predetermined photoelectric conversion processing. An image pickup signal obtained in this manner is inputted to the control processor 9 through the signal cable 40. The control processor 9 subjects the inputted image pickup signal to various kinds of signal processing, and outputs an image signal that is generated as a result of the signal processing to the display apparatus 11. The display apparatus 11 that receives the image signal displays an endoscopic image corresponding thereto.

FIG. 5 is a view illustrating a display example of an endoscopic image that is displayed on the display apparatus 11 in accordance with an image signal obtained by the endoscope 1 of the present embodiment. As shown in FIG. 5, an image display region 11c in which an endoscopic image is displayed and an information display region 11d in which various kinds of information are displayed and the like exist on the display monitor of the display apparatus 11. Of these regions, a substantially circular endoscopic image is displayed in the image display region 11c. In the endoscopic image, an observation image of the front field of view is displayed in a circular region 11a on the inner side, and an observation image of the lateral field of view is displayed in an annular region 11b at a peripheral portion of the circular region 11a.

Note that, with respect to the other detailed configuration of the endoscope 1, it is assumed that a similar configuration to the configuration applied in a conventional endoscope of the same type is adopted, and hence a description and illustration thereof are omitted here.

An outline of operations when performing endoscopic observation of a luminal organ such as the large intestine using the endoscope 1 of the present embodiment configured in this manner will now be described mainly using FIG. 4.

First, the insertion portion 2 of the endoscope 1 is inserted into a luminal organ or the like by a normal procedure. It is assumed that the distal end portion 6 of the endoscope 1 is thereby positioned as shown in FIG. 4. In this state, the detection circuit 9a of the control processor 9 receives signals from the photometric sensors 41 and 42, and performs an operation to calculate a distance (first distance) from the front observation-use objective lens 21 to an observation target in front of the distal end portion 6 and a distance (second distance) from the lateral observation-use objective lens 22 to an observation target at the side of the distal end portion 6 based on the respective items of photometric information that were detected. Here, the distance from the photometric sensor 41 to the observation target in front of the distal end portion 6 is taken as LA, and the distance from the photometric sensor 42 to the observation target at the side of the distal end portion 6 is taken as LB.

Next, the control circuit 9b subjects the light amount varying mechanism 45 to driving control based on the distance information (LA and LB) calculated by the detection circuit 9a, and thereby sets a rotational position around the axis of the distal-end-side end face 32aa of the second light guide 32a.

For example, in a case where a distance LA/LB is greater than a predetermined threshold value T, it can be considered that although the front observation-use objective lens 21 and a front observation target 101a are at positions that are separated from each other, the lateral observation-use objective lens 22 and a lateral observation target 101b are at positions that are close to each other. In this case, on the display screen of the display apparatus 11 shown in FIG. 5, an image displayed in the image region for an observation image 11a of the front field of view is darker than an image displayed in the image region for an observation image 11b of the lateral field of view. Therefore, in a case where $$LA/LB > T,$$

the control circuit 9b subjects the light amount varying mechanism 45 to driving control to rotationally control the second light guide 32a so that the inclined face of the distal-end-side end face 32aa of the second light guide 32a faces inward (state shown in FIG. 6). By increasing the amount of illuminating light irradiated toward the front of the distal end portion 6 relative to the amount of illuminating light irradiated toward the side of the distal end portion 6 in this manner, the brightness of the observation image 11a of the front field of view is improved. Accordingly, since light can be distributed so as to achieve an appropriate balance between the amount of illuminating light irradiated to the front field of view and the amount of illuminating light irradiated to the lateral field of view, substantially uniform images are displayed in the image regions of the observation images 11a and 11b on the display screen.

Further, for example, in a case where the distance LA/LB is less than the predetermined threshold value T, it can be considered that although the front observation-use objective lens 21 and the front observation target 101a are at positions that are close to each other, the lateral observation-use objective lens 22 and the lateral observation target 101b are at positions that are separated from each other. In this case, on the display screen of the display apparatus 11 shown in FIG. 5, an image displayed in the image region for the observation image 11b of the lateral field of view is darker than an image displayed in the image region for the observation image 11a of the front field of view. Therefore, in a case where $$LA/LB<T,$$

the control circuit 9b subjects the light amount varying mechanism 45 to driving control to rotationally control the second light guide 32a so that the inclined face of the distal-end-side end face 32aa of the second light guide 32a faces outward (state shown in FIG. 7). By increasing the amount of illuminating light irradiated toward the side of the distal end portion 6 relative to the amount of illuminating light irradiated toward the front of the distal end portion 6 in this manner, the brightness of the observation image 11b of the lateral field of view is improved. Accordingly, since light can be distributed so as to achieve an appropriate balance between the amount of illuminating light irradiated to the front field of view and the amount of illuminating light irradiated to the lateral field of view, substantially uniform images are displayed in the image regions of the observation images 11a and 11b on the display screen.

Thus, the control circuit 9b that is a control portion determines the proportions of the amount of illuminating light to be emitted to the front of the front observation-use objective lens 21 (first objective lens) and the amount of illuminating light to be emitted to the side of the lateral observation-use objective lens 22 (second objective lens) based on the ratio between the first distance and the second distance, and controls the light amount varying mechanism 45 (light amount varying means).

Note that, for example, a value that is stored as previously set data in a storage portion (not shown) that is data storage means provided inside the control processor 9 is used as the aforementioned threshold value T. In this case, the storage portion is a constituent portion that stores threshold values relating to ratios for respective distances between an object to be observed and the respective objective lenses 21 and 22.

According to the first embodiment as described above, a configuration is adopted which includes the photometric sensor 41 that receives reflected light from an observation target in front of the distal end portion 6 of the insertion portion 2 of the endoscope 1 and measures the amount of reflected light that is received; the first distance detection portion constituted by the detection circuit 9a that calculates a distance (first distance) between the front observation-use objective lens 21 (first objective lens) and an observation target that is in front of the front observation-use objective lens 21 based on a detection result (front photometric information) obtained by the photometric sensor 41; the photometric sensor 42 that receives reflected light from an observation target at the side of the distal end portion 6 of the insertion portion 2 of the endoscope 1 and measures the amount of reflected light that is received; and the second distance detection portion constituted by the detection circuit 9a that calculates a distance (second distance) between the lateral observation-use objective lens 22 (second objective lens) and an observation target that is at the side of the lateral observation-use objective lens 22 based on a detection result (lateral photometric information) obtained by the photometric sensor 42; and which also includes: the lateral illumination lens 32 (light distribution member) formed in a shape such that the lateral illumination lens 32 is capable of distributing and irradiating light from the second light guide 32a among the plurality of light guides that guide illuminating light emitted from the light source apparatus 10 to the distal end side of the insertion portion 2 of the endoscope 1 to the front of the front observation-use objective lens 21 (first objective lens) and to the side of the lateral observation-use objective lens 22 (second objective lens); and the light amount varying mechanism 45 that is light amount varying means for changing proportions of light amounts with respect to illuminating light emitted to the front of the front observation-use objective lens 21 (first objective lens) and illuminating light emitted to the side of the lateral observation-use objective lens 22 (second objective lens); and which further includes: the control circuit 9b that controls the light amount varying mechanism 45 based on a signal relating to a first distance (a distance between the front observation-use objective lens 21 (first objective lens) and an observation target in front of the front observation-use objective lens 21) that is calculated and outputted by the detection circuit 9a based on information obtained by the photometric sensor 41, and a signal relating to a second distance (a distance between the lateral observation-use objective lens 22 (second objective lens) and an observation target that is to the side of the lateral observation-use objective lens 22) that is calculated and outputted by the detection circuit 9a based on information obtained by the photometric sensor 42.

It is thereby possible to perform control to rotate a predetermined region in the vicinity of the distal end portion of the second light guide 32a by a predetermined rotation amount at a predetermined timing to change the emission angle of illuminating light that is made incident on the lateral illumination lens 32 from the second light guide 32a, and thus control the amounts of illuminating light emitted to the front field of view and the lateral field of view. Accordingly, with respect to endoscopic images to be displayed on the display screen of the display apparatus 11, it is possible to always display an observation image of a front field of view and an observation image of a lateral field of view with a uniform brightness.

Second Embodiment

Next, an endoscope according to a second embodiment of the present invention will be described. The fundamental configuration of the present embodiment is substantially the same as that of the above described first embodiment. In the present embodiment, the configurations of the front illumination unit and the lateral illumination unit among the plurality of illumination units are different from the respective configurations in the above described first embodiment. Therefore, components that are the same as in the first embodiment are denoted by the same reference numerals. Further, a detailed description and illustration of components that are the same as in the above described first embodiment is omitted hereunder, and only components that are different from those of the first embodiment are described in detail.

Note that, with respect to omitted drawings relating to the second embodiment, the drawings used for the description of the foregoing first embodiment are referred to in the following description.

Figure 8:
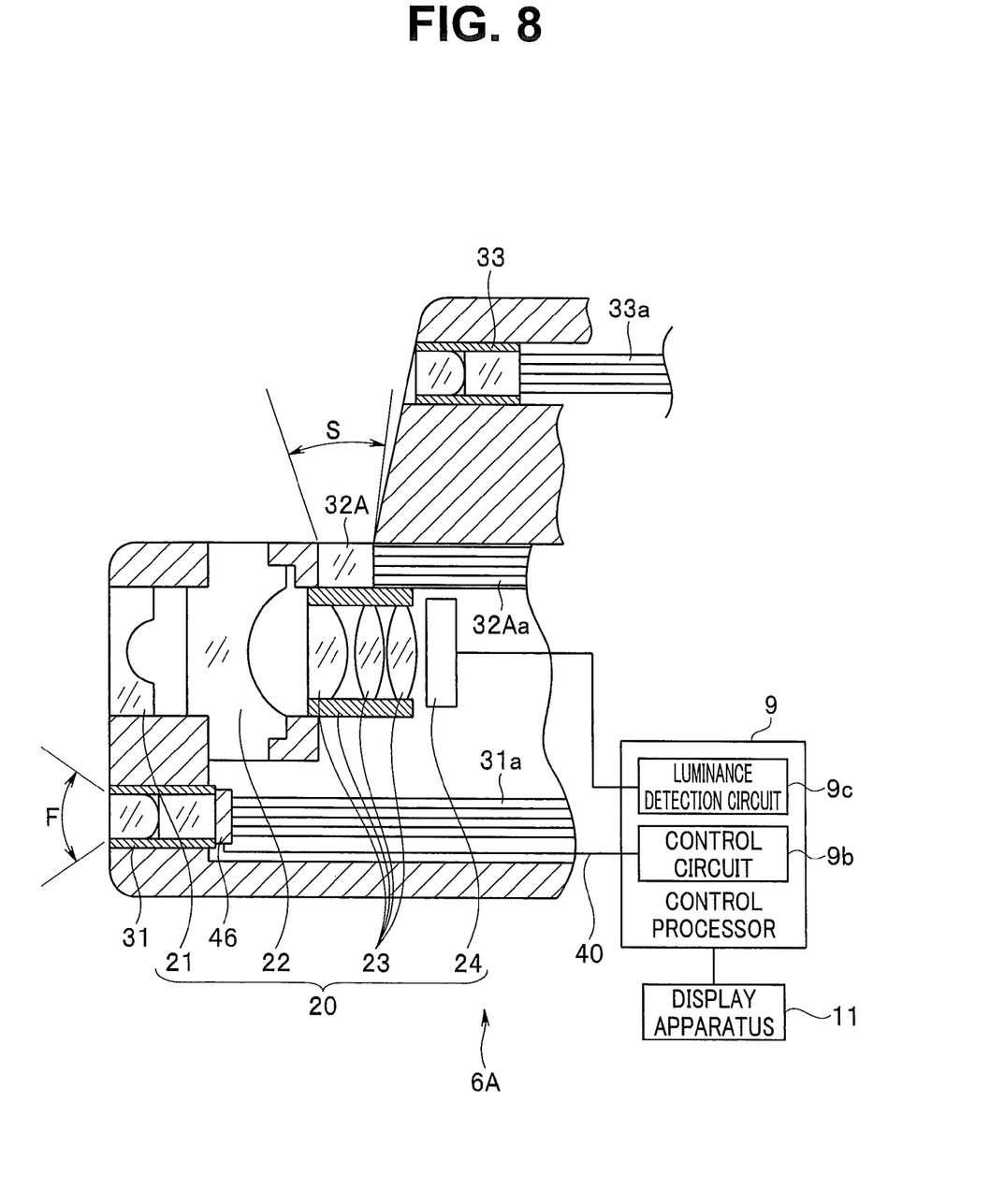
FIG. 8 is a cross-sectional view of the vicinity of a distal end portion in an endoscope according to a second embodiment of the present invention.

FIG. 8 is a cross-sectional view of the vicinity of a distal end portion of an endoscope according to the second embodiment of the present invention. Note that FIG. 8 corresponds to FIG. 4 in the above described first embodiment and illustrates a cross section at a site in the endoscope of the present embodiment that corresponds to the site along the line [4]-[4] in FIG. 3 that is described in the foregoing first embodiment.

The configurations of the endoscope of the present embodiment and the overall endoscope system that includes the endoscope of the present embodiment are substantially the same as in the foregoing first embodiment (see FIG. 1).

As shown in FIG. 8, the image pickup unit 20 and a plurality of illumination units, namely, a front illumination unit, a lateral illumination unit, and a front auxiliary illumination unit and the like are principally arranged inside a distal end portion 6A of the insertion portion 2 of the endoscope of the present embodiment.

The configurations of the image pickup unit 20 and the front auxiliary illumination unit (33, 33a) are completely the same as in the above described first embodiment.

On the other hand, the front illumination unit in the endoscope of the present embodiment is constituted by the front illumination lens 31, the first light guide 31a, and a light adjustment member 46 that is light amount varying means and the like.

The light adjustment member 46 is arranged in the optical path of light irradiated in the observation direction (that is, to the front of the distal end portion 6A) by the front observation-use objective lens 21 (first objective lens), that is, the light adjustment member 46 is arranged between the front illumination lens 31 and the first light guide 31a. The light adjustment member 46 is a member that changes a proportion of illuminating light emitted from the light guide that is transmitted therethrough to thereby adjust the light. For example, an electrochromic device that is a light-adjusting glass is applied as the light adjustment member 46.

The light adjustment member 46 is electrically connected to the control circuit 9b inside the control processor 9 through the signal cable 40.

A luminance detection circuit 9c is also provided inside the control processor 9. The luminance detection circuit 9c calculates luminance data of each image region formed by the respective objective lenses (21, 22) in images that are displayed on a monitor screen of the display apparatus 11 that are respectively acquired by the objective lenses (21, 22) based on output signals (image signals) from the image pickup unit 20.

For example, although not particularly illustrated in the drawings, the luminance detection circuit 9c includes a first light amount detection portion that detects the reflection intensity (luminance) of illuminating light emitted to the front of the front observation-use objective lens 21 (first objective lens), and a second light amount detection portion that detects the reflection intensity (luminance) of illuminating light emitted to the side of the lateral observation-use objective lens 22 (second objective lens). The first light amount detection portion detects a light amount in a substantially center region 11a (that is, the region of a front image) in an endoscopic image (circular image displayed in the image display region 11c of the display apparatus 14; see FIG. 5) at a time that images of the respective objects to be observed in the front and at the side of the distal end portion 6A of the insertion portion 2 that are picked up by the endoscope are displayed as images on the display apparatus 14. Further, the second light amount detection portion detects a light amount in a predetermined region, for example, an outer edge region 11b (that is, the region of a lateral image), that is on the outer side relative to the center region of the same endoscopic image.

Thus, the control circuit 9b subjects the light adjustment member 46 to driving control based on luminance data acquired by the luminance detection circuit 9c. That is, the control circuit 9b adjusts the amount of illuminating light from the first light guide 31a that is transmitted through the light adjustment member 46.

In other words, based on a first light amount (light amount and luminance of front image) that the first light amount detection portion detected and a second light amount (light amount and luminance of lateral image) that the second light amount detection portion detected, the control circuit 9b determines the proportions of light amounts with respect to illuminating light to be emitted to the front of the front observation-use objective lens 21 (first objective lens) and illuminating light to be emitted to the side of the lateral observation-use objective lens 22 (second objective lens), and subjects the light adjustment member 46 that is the light amount varying means to driving control.

Further, the lateral illumination unit of the present embodiment is constituted by a lateral illumination lens 32A such as a prism and a second light guide 32Aa. The second light guide 32Aa is provided parallel to the axial direction of the distal end portion 6A, and illuminating light is emitted from the distal-end-side end face of the second light guide 32Aa. In this case, the distal-end-side end face of the second light guide 32Aa is formed as a plane that is substantially orthogonal to the axial direction.

A light incidence face of the lateral illumination lens 32A is provided substantially parallel to the distal-end-side end face of the second light guide 32Aa at a site facing the distal-end-side end face. The lateral illumination lens 32A is configured so that the travelling direction of illuminating light that is incident thereon is changed by a light scattering face inside the lateral illumination lens 32A so that the illuminating light is emitted in a predetermined irradiation region S at the side of the distal end portion 6A.

Note that the light amount varying mechanism 45, the photometric sensors 41 and 42 and the detection circuit 9c and the like of the above described first embodiment are omitted from the configuration of the present embodiment. The remaining configuration is substantially the same as in the above described first embodiment.

In the present embodiment configured as described above, for example, when an average luminance of the front field of view (first light amount) that is represented by "A" and an average luminance of the lateral field of view (second light amount) that is represented by "B" are measured by the luminance detection circuit 9c, in a case where $$A/B > \text{threshold value } T2,$$

it can be considered that the observation target in the front field of view is at a nearer position than the observation target in the lateral field of view. Therefore, in this case, the control circuit 9b performs voltage control to lower the transmittance of the light adjustment member 46. As a result, the light amount balance between the front field of view and the lateral field of view is made the appropriate balance as a result of the amount of illuminating light irradiated to the front field of view decreasing.

On the other hand, in a case where $$A/B > \text{threshold value } T2,$$

it can be considered that the observation target in the front field of view is at a position that is further away than the observation target in the lateral field of view. Therefore, in this case, the control circuit 9b performs voltage control to increase the transmittance of the light adjustment member 46. As a result, the amount of illuminating light irradiated to the front field of view increases and the light amount balance between the front field of view and the lateral field of view is made the appropriate balance.

Thus, in the present embodiment, driving control of the light adjustment member 46 is performed based on the magnitude relationship between a ratio (A/B) between the first light amount A and the second light amount B and the threshold value T2.

Note that, in the present embodiment, for example, a value that is stored as previously set data in a storage portion (not shown) that is data storage means provided inside the control processor 9 is used as the aforementioned threshold value T2. That is, the storage portion is a constituent portion that stores threshold values relating to ratios between the first light amount and the second light amount.

As described above, similar effects as those in the foregoing first embodiment can be obtained according to the second embodiment. In addition, in the present embodiment, a simple configuration is adopted in which the light adjustment member 46 is disposed between an illumination lens and a light guide, and a control circuit is provided that subjects the light adjustment member 46 to driving control. Accordingly, the configuration of present embodiment can contribute to improvement of assemblability and reduction of the manufacturing cost.

Note that although an example in which the light adjustment member 46 is provided between the front illumination lens 31 and the first light guide 31a is described in the present embodiment, the present invention is not limited thereto. For example, the same effects can also be obtained by substantially the same actions in the case of a configuration in which the light adjustment member 46 is provided in the optical path of light irradiated in the observation direction (that is, toward the side of the distal end portion 6A) by the lateral observation-use objective lens 22 (second objective lens).

Third Embodiment

Next, an endoscope according to a third embodiment of the present invention will be described. The fundamental configuration of the present embodiment is substantially the same as that of the above described first and second embodiments. In the present embodiment, the configuration of the lateral illumination unit among the plurality of illumination units is different from the configuration thereof in the above described second embodiment. Accordingly, components that are the same as in the foregoing first and second embodiments are denoted by the same reference numerals. Further, a detailed description and illustration of components that are the same as in the above described first and second embodiments are omitted hereunder, and only components that are different from the first and second embodiments are described in detail. Note that, with respect to omitted drawings relating to the third embodiment, the drawings used for the description of the foregoing first embodiment are referred to in the following description.

Figure 9:
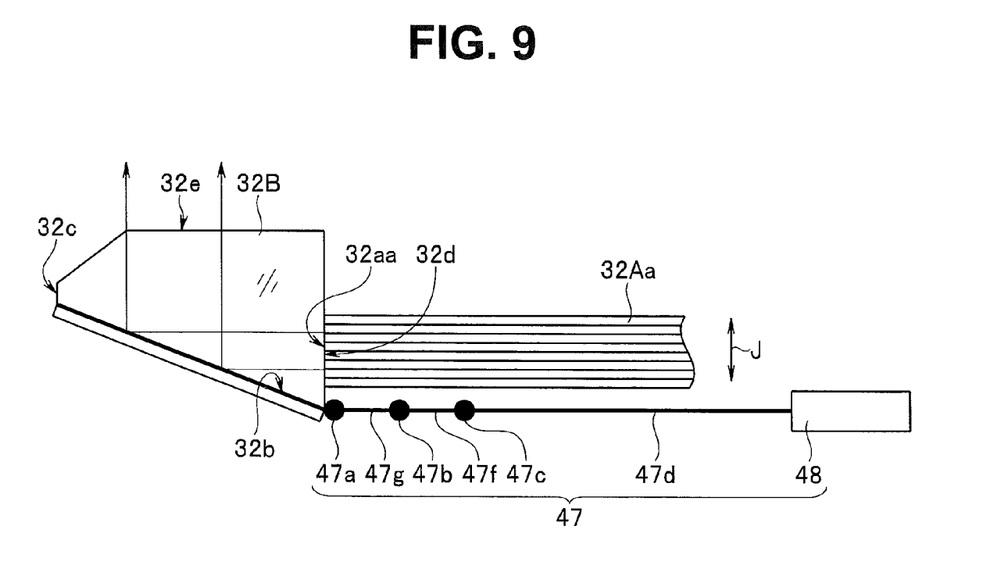
FIG. 9 is a schematic configuration diagram of a lateral illumination unit in an endoscope according to a third embodiment of the present invention, that shows the arrangement of a light guide when performing normal lateral irradiation.
Figure 10:
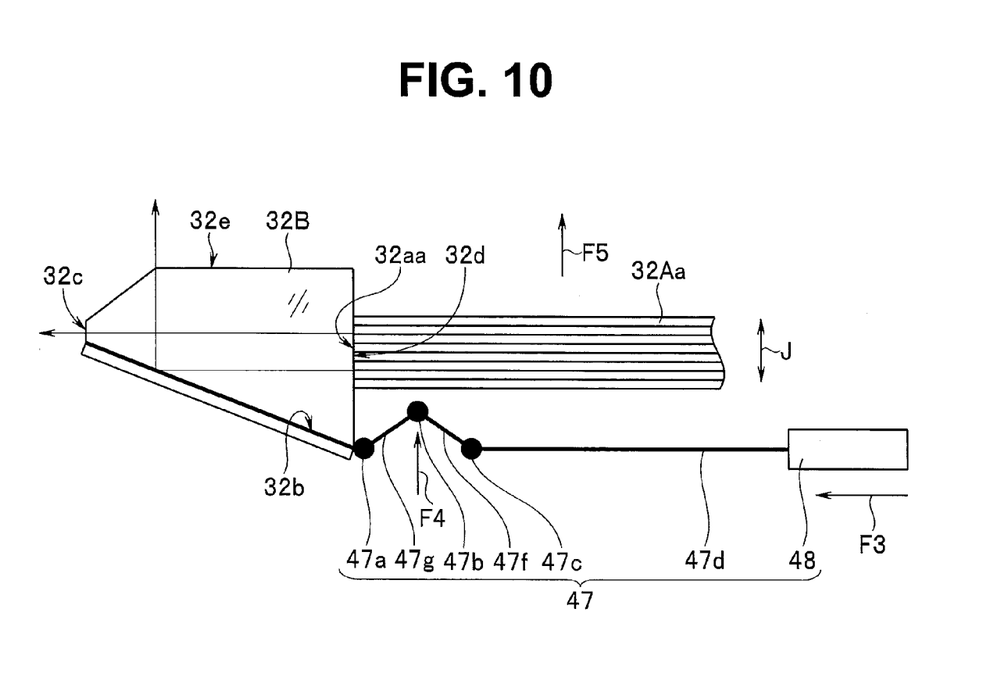
FIG. 10 is a schematic configuration diagram of the lateral illumination unit shown in FIG. 9, that shows the arrangement of the light guide when irradiating part of an illuminating light frontward using the lateral illumination unit.

FIG. 9 and FIG. 10 are conceptual diagrams that illustrate the schematic configuration of the lateral illumination unit in the endoscope of the third embodiment of the present invention in a state in which the lateral illumination unit has been taken out therefrom. FIG. 9 is a schematic configuration diagram of the lateral illumination unit that illustrates the arrangement of a light guide when performing normal lateral irradiation using a lateral illumination lens. FIG. 10 is a schematic configuration diagram of the lateral illumination unit that illustrates the arrangement of the light guide when also irradiating part of the illuminating light frontward using the lateral illumination lens.

The configurations of the endoscope of the present embodiment and the overall endoscope system that includes the endoscope of the present embodiment are substantially the same as in the foregoing first and second embodiments (see FIG. 1). Further, the internal configuration of the distal end portion of the insertion portion of the endoscope is also substantially the same as in the above described first and second embodiments. Note that, the light amount varying mechanism 45, the photometric sensors 41 and 42 and the detection circuit 9c and the like of the above described first embodiment are omitted from the configuration of the present embodiment.

Further, as shown in FIG. 9, the lateral illumination unit provided inside the distal end portion of the insertion portion of the endoscope of the present embodiment is constituted by a lateral illumination lens 32B, the second light guide 32Aa, a light amount varying mechanism 47 that is light amount varying means and the like.

Similarly to the above described first embodiment, the lateral illumination lens 32B is constituted by a prism composed of a polyhedron having at least the light incidence face 32d, the front emission face 32c, the lateral emission face 32e, and the light scattering face 32b.

Similarly to the above described second embodiment, the second light guide 32Aa is provided in parallel with the axial direction of the distal end portion of the endoscope insertion portion, and an illuminating light is emitted from the distal-end-side end face of the second light guide 32Aa. In this case, the distal-end-side end face of the second light guide 32Aa is formed as a plane that is substantially orthogonal to the axial direction. The second light guide 32Aa is arranged so as to be movable in a direction (arrow J direction shown in FIG. 9 and FIG. 10) that is orthogonal to the axial direction of the distal end portion of the endoscope insertion portion upon being subjected to an action (described later) of the light amount varying mechanism 47. That is, the distal-end-side end face of the second light guide 32Aa is configured to be movable in the aforementioned arrow J direction along the light incidence face of the lateral illumination lens 32B.

The light incidence face 32d of the lateral illumination lens 32B is provided substantially parallel to the distal-end-side end face of the second light guide 32Aa at a site facing the distal-end-side end face. The lateral illumination lens 32B is configured so that, when the light amount varying mechanism 47 is in a normal state (state shown in FIG. 9), the travelling direction of illuminating light that is incident thereon is changed by the light scattering face 32b inside the lateral illumination lens 32B so that the illuminating light is emitted from the lateral emission face 32e and is emitted in an irradiation range that is at the side of the endoscope. Further, the lateral illumination lens 32B is configured so that, in a state in which the light amount varying mechanism 47 has acted (state illustrated in FIG. 10), in addition to illuminating light whose course was changed by the light scattering face 32b inside the lateral illumination lens 32B so as to be emitted from the lateral emission face 32e, some of the illuminating light incident on the lateral illumination lens 32B travels in a straight line and is emitted from the front emission face 32c.

As shown in FIG. 9 and FIG. 10, the light amount varying mechanism 47 is constituted by a fixing pin 47a, a plurality of joints (47b and 47c), two link shafts (47f and 47g) that are connected in series by the plurality of joints (47b and 47c), a driving link 47d, a driving source 48, and a control circuit thereof (included in the control processor 9) and the like.

The action of the light amount varying mechanism 47 is as follows. The control circuit included in the control processor 9 performs driving control of the driving source 48. In this case, the driving control of the driving source 48 is, for example, performed in accordance with the same conditions as the control conditions that are determined based on luminance data acquired by the luminance detection circuit 9c in the above described second embodiment.

In a normal case, the light amount varying mechanism 47 is in the state illustrated in FIG. 9. In this state, illuminating light emitted from the second light guide 32Aa is emitted towards only the side of the distal end portion of the endoscope insertion portion through the lateral illumination lens 32B.

On the other hand, under a predetermined condition, the driving source 48 is subjected to driving control, and the driving link 47d is pressed in the direction of an arrow F3 shown in FIG. 10. Thereupon, as shown in FIG. 10, the proximal end side link 47f that is connected to the driving link 47d through the joint 47c, and the distal end side link 47g that is connected through the joint 47b with the proximal end side link 47f causes the joint 47b to move in the direction of an arrow F4. As a result, the joint 47b causes the second light guide 32Aa to move in the direction of an arrow F5 along the arrow J direction.

Thus, the configuration is such that by controlling driving of the driving source 48 by means of the control circuit, relative to the state shown in FIG. 9, that is, a state in which all of the illuminating light emitted from the second light guide 32Aa is irradiated to the side, a state can be entered in which some of the illuminating light is allocated to front irradiation, and furthermore, an increase or decrease in the amount of light allocated to front irradiation can be controlled by controlling the position of the second light guide 32Aa in the arrow J direction. The remaining configuration is substantially the same as in the above described first and second embodiments.

According to the third embodiment that is described above, the same effects as in the above described second embodiment can be obtained. Note that, in the present embodiment, a simple link mechanism is used to construct the light amount varying mechanism 47. It is thereby possible to contribute to a reduction in the size and weight of the apparatus, and at the same time to also contribute to decreasing the manufacturing cost and improving the manufacturing technology.

Note that the present invention is not limited to the above described embodiments, and naturally various modifications and applications can be implemented within a range that does not deviate from the gist of the present invention. Further, the above described embodiments include inventions of various stages, and various inventions can be extracted by appropriately combining a plurality of the disclosed configuration requirements. For example, if a problem to be solved by the invention can be solved and the effects of the invention are obtained even after omitting some of the configuration requirements from the entire configuration requirements described in the respective embodiments described above, then the configuration obtained by omitting the configuration requirements can be extracted as an invention.

INDUSTRIAL APPLICABILITY

The present invention can be applied not just to an endoscope control apparatus in the medical field, but also to an endoscope control apparatus in the industrial field.

What is claimed is:

1. An endoscope comprising:
a first objective lens that is disposed in an insertion portion to be inserted into a lumen, and forms an image of an object to be observed that is in a first observation direction;
a second objective lens that is disposed in the insertion portion, and forms an image of an object to be observed that is in a second observation direction that is different from the first observation direction;
a light guide that guides an illuminating light that is emitted from a light source to the insertion portion;
a light distribution member that distributes light from the light guide between the first observation direction and the second observation direction;
light amount varying means for changing proportions of light amounts with respect to illuminating light emitted in the first observation direction and illuminating light emitted in the second observation direction that the light distribution member distributes;
a distance detection portion that measures a second distance between the second objective lens and an object to be observed that is in the second observation direction; and
a control portion that controls the light amount varying means based on a signal relating to the second distance that is outputted from the distance detection portion.

2. The endoscope according to claim 1, wherein:
the distance detection portion further measures a first distance between the first objective lens and an object to be observed that is in the first observation direction; and
the control portion controls the light amount varying means based on a signal relating to the first distance that is outputted from the distance detection portion and a signal relating to the second distance that is outputted from the distance detection portion.

3. The endoscope according to claim 2, wherein:
the control portion determines the proportions of light amounts with respect to the illuminating light emitted in the first observation direction and the illuminating light emitted in the second observation direction based on a ratio between the first distance and the second distance, and controls the light amount varying means.

4. The endoscope according to claim 3, wherein:
the control portion comprises a storage portion that stores a threshold value relating to a ratio between respective distances between objects to be observed and the respective objective lenses; and
when the first distance is taken as LA, the second distance is taken as LB, and a threshold value is taken as T, the control portion controls the light amount varying means based on a magnitude relationship between LA/LB and T.

5. The endoscope according to claim 2, wherein:
the distance detection portion comprises:
a first distance detection portion that measures a first distance between the first objective lens and an object to be observed that is in front of the first objective lens; and
a second distance detection portion that measures a second distance between the second objective lens and an object to be observed that is to a side of the second objective lens.

6. The endoscope according to claim 5, further comprising:
a first light amount detection portion that measures a light amount of first reflected light as reflected light from an object to be observed that is in the first observation direction; and a second light amount detection portion that measures a light amount of second reflected light as reflected light from an object to be observed that is in the second observation direction, wherein, the first distance detection portion measures the first distance based on information relating to a first light amount that is the light amount of the first reflected light detected by the first light amount detection portion, the second distance detection portion measures the second distance based on information relating to a second light amount that is the light amount of the second reflected light detected by the second light amount detection portion, and based on information relating to the first distance from the first distance detection portion and information relating to the second distance from the second distance detection portion, the control portion determines proportions of light amounts with respect to the illuminating light emitted in the first observation direction and the illuminating light emitted in the second observation direction and controls the light amount varying means.

7. The endoscope according to claim 6, wherein:

the control portion comprises a storage portion that stores a threshold value relating to a ratio between the first light amount and the second light amount; and the control portion controls the light amount varying means based on a magnitude relationship between a value of the first light amount/the second light amount and the threshold value.

8. The endoscope according to claim 6, wherein:

the first light amount detection portion detects a light amount in a center region of an endoscopic image obtained by forming images of the respective objects to be observed that the endoscope picks up; and the second light amount detection portion detects a light amount in a predetermined region that is located further on an outer side than the center region of the endoscopic image.

9. The endoscope according to claim 1, wherein:

the first objective lens is disposed on a distal end side of the insertion portion, and forms an image of an object to be observed that is in front of the insertion portion; and the second objective lens is disposed on a lateral side of the insertion portion, and forms an image of an object to be observed that is to a side of the insertion portion.

10. The endoscope according to claim 9, wherein:

the light distribution member distributes light from the light guide to the front of the first objective lens and to the side of the second objective lens.

11. The endoscope according to claim 9, wherein:

the second objective lens includes a circular lens that is disposed at a position that is further on a proximal end side of the insertion portion than the first objective lens.

12. The endoscope according to claim 1, wherein:

the light distribution member comprises a light scattering portion that changes proportions of the illuminating light distributed in the first observation direction and in the second observation direction according to an angle of incidence of light from the light guide; and the light amount varying means further comprises an actuator that rotates the light guide in which an angle at which illuminating light is emitted is changed.

13. The endoscope according to claim 1, wherein:

the light distribution member comprises a light scattering portion that changes proportions of the illuminating light distributed in the first observation direction and in the second observation direction according to a position at which the illuminating light is incident from the light guide; and the light amount varying means includes a mechanism that moves a position of the light guide relative to the light distribution member, a driving source that drives the mechanism, and a control circuit that performs driving control of the driving source.

* * * * *